United States Patent [19]

Steiner et al.

[11] Patent Number: 5,843,295
[45] Date of Patent: Dec. 1, 1998

[54] GEL ELECTROPHORESIS WELL-FORMING AND LOADING-GUIDE COMB

[75] Inventors: Urs Steiner, Sunnyvale; Tim O. Lau, Fremont; Terry A. Landers, Moraga, all of Calif.

[73] Assignee: Pharmacia Biotech, San Francisco, Calif.

[21] Appl. No.: 992,928

[22] Filed: Dec. 18, 1997

Related U.S. Application Data

[60] Provisional application No. 60/033,677 Dec. 19, 1996.
[51] Int. Cl.$^6$ .............................. G01N 27/26; C12M 3/00
[52] U.S. Cl. ....................... 204/619; 204/620; 435/288.4; 435/309.1
[58] Field of Search ..................................... 204/456, 465, 204/466, 467, 66, 615, 616, 618, 619, 620; 132/161, 139, 901; 435/288.4, 305.2, 309.4, 309.1, 73

[56] References Cited

U.S. PATENT DOCUMENTS

| | | |
|---|---|---|
| 4,909,918 | 3/1990 | Bamback et al. . |
| 5,284,565 | 2/1994 | Chu et al. ................................ 204/299 |
| 5,407,552 | 4/1995 | Lebacq . |
| 5,411,657 | 5/1995 | Leka . |
| 5,618,399 | 4/1997 | Gautsch et al. ......................... 204/620 |
| 5,656,145 | 8/1997 | Nguyen et al. . |

OTHER PUBLICATIONS

Pharmacia Biotech Biodirectory catalog, 298, 301, 309–312 (1997).

*Primary Examiner*—Robert J. Warden
*Assistant Examiner*—Alex Noguerola
*Attorney, Agent, or Firm*—Lyon & Lyon LLP

[57] ABSTRACT

A well-forming and loading-guide comb for electrophoresis gels. The comb includes a comb body, to which well-forming teeth and a loading guide are attached in an opposing fashion. The comb can be used with the teeth pointing downward into the gel to form sample wells in either vertical or horizontal electrophoresis gels. Upon hardening of the gel, the comb is once removed from the gels, leaving sample wells therein. The comb is then rotated 180 degrees, and notches (in the case of vertical electrophoresis gels) or L-shaped extensions (in the case of horizontal electrophoresis gels) of the loading guide are aligned with the sample wells so as to provide for easy guided access of a sample delivering instrument during the loading of samples into the wells.

6 Claims, 5 Drawing Sheets

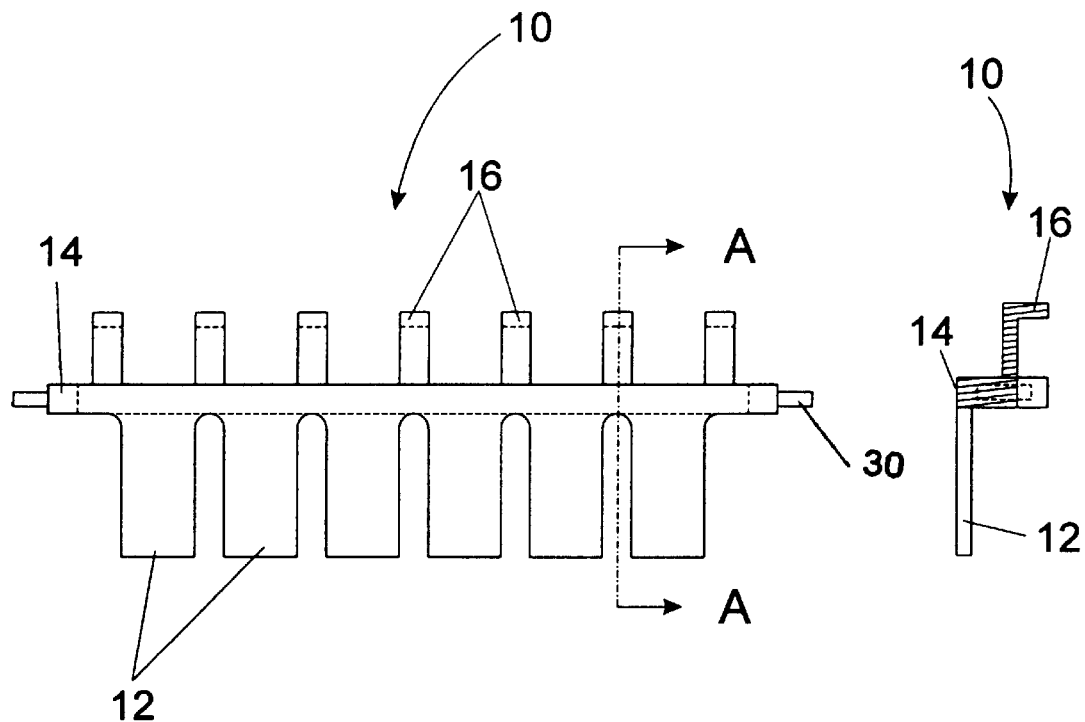
Figure 6A
Figure 6B
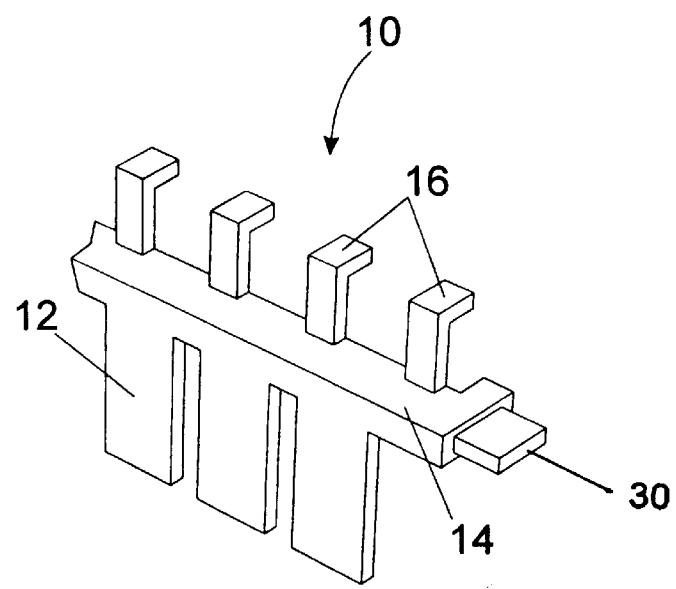
Figure 7

GEL ELECTROPHORESIS WELL-FORMING AND LOADING-GUIDE COMB

This application claims the benefit of U.S. Provisional Application No. 60/033,677, filed Dec. 19, 1997.

BACKGROUND OF THE INVENTION

1. Field of the Invention

The present invention relates to gel electrophoresis apparatus and in particular to a well-forming and loading-guide comb for electrophoresis gels.

2. Description of the Related Art

Gel electrophoresis is a technique used to separate and analyze molecules present in complex liquid mixtures. The separation and analysis are based on the migration of the molecules through a gel while under an applied electric field. When exposed to such an electric field, each molecule will migrate to the pole that carries a charge opposite to that of the molecule. In addition, since the migration takes place in a porous gel, the speed of migration will depend on the size of a molecule, with smaller molecules traveling faster than larger molecules. Gel electrophoresis, therefore, can separate molecules according to both their size and their charge.

There are two general types of gel electrophoresis apparatus, those in which the gel is in the form of a vertical slab and those in which the gel is in the form of a horizontal slab. The details of both of these types of apparatus are widely known in the field.

Casting of vertical electrophoresis gels, e.g. those of polyacrylamide or agarose, is commonly done by creating a cassette formed of two plates separated by spacers at the edges. The bottom of the cassette may be sealed by tape, another spacer, or compression against a gasket. Once the cassette is formed and sealed on the edges and bottom, a gel solution of, for example, acrylamide, polymerization catalysts and buffers is poured into the cassette and allowed to polymerize (i.e. harden) into a gel. Prior to complete hardening of the solution, a "comb" structure with "teeth" is often inserted into the solution. The solution then hardens into a gel around the teeth. The comb is subsequently withdrawn from the gel, leaving a series of sample wells in the gel surface. Liquid mixtures to be analyzed are loaded into the well, typically using a pipette, syringe needle or similar sample delivering instrument.

The procedures for casting and loading a horizontal electrophoresis gel are similar to the aforementioned procedure for vertical electrophoresis gels, with a difference being that the gel is cast in a tray-like support instead of a vertical cassette. Sample wells are again formed in the upper surface of the gel.

Electrophoresis gels are typically highly transparent. If a transparent cassette or tray is used in a transparent electrophoresis unit, the location of sample wells within the gel may be detectable due to the differences in refraction of distant objects viewed through the gel compared to an empty well. But, such detection is not always easy, and is occasionally impossible. More frequently than not, the sample wells are difficult to identify, particularly when an opaque electrophoresis unit or gel support plate is used and the wells are initially filled with liquid. This difficulty in locating the sample wells makes loading of a liquid sample into the well onerous, possibly causing sample misplacement, time loss, or damage to the gel from the loading instrument, possibly resulting in erroneous data.

While combs for forming sample wells in electrophoresis gels are known (see Pharmacia Biotech *Biodirectory '97* catalog, 298, 301, 309–312; U.S. Pat. No. 5,407,552 to Lebacq and U.S. Pat. No. 5,411,657 to Leka, each of which is incorporated herein by reference), these conventional combs are removed after the wells have been formed and therefore provide no guidance to the user in locating a well for sample placement. U.S. Pat. No. 4,909,918 to Bambeck et al. also describes a disposable comb for gel electrophoresis. The Bambeck comb, however, provides for wells on the gel rather than in the gel.

U.S. Pat. No. 5,656,145 to Nguyen et al. describes a needle guide for loading electrophoresis samples. The needle guide of Nguyen requires a separate well-forming insert, i.e. comb, to construct a series of wells along the top of a gel slab. U.S. Pat. No. 5,324,412 to Kolner describes an apparatus that employs grooves ground into a vertical cassette plate to aid in sample loading. The apparatus of Kolner, however, requires a separate comb for constructing the sample wells and there is no choice in the number of wells without manufacturing a different vertical cassette plate. Further, it is preferable that such an apparatus be inexpensive enough to be disposable after one use as a preferred means of avoiding any carryover contamination of subsequently loaded samples.

Still needed in the art is an apparatus that can both form sample wells in an electrophoresis gel and provide guidance to a user in loading those sample wells with a solution to be analyzed.

SUMMARY OF THE INVENTION

The present invention provides a combination well-forming and loading-guide comb for electrophoresis gels. The comb is used both to form sample wells in an electrophoresis gel and as a guide in the loading of liquid samples into these wells.

The comb includes a comb body having two opposing edges, a plurality of sample-well-forming teeth and a loading guide for guiding the loading of samples into the wells formed in an electrophoresis gel by the sample-well-forming teeth. The sample-well-forming teeth and the loading guide are connected to opposite edges of the comb body.

For use with a vertical electrophoresis gel (one embodiment), the comb body is sized and shaped to fit between two plates of a vertical gel electrophoresis cassette that are spaced apart in an overlying relationship. The plurality of sample-well-forming teeth are connected to the comb body along one edge thereof, while the loading guide is connected to the opposite edge. The loading guide includes a flat plate with a plurality of loading alignment notches that are designed to align with a plurality of sample wells formed in the gel by the sample-well-forming teeth.

For use with horizontal electrophoresis gels (a second embodiment), the comb body is sized and shaped to engage a horizontal gel casting support tray in a manner that reproducibly aligns the comb to the gel. The comb body includes bottom and top faces, with the plurality of sample-well-forming teeth connected to the comb body along its bottom face and the loading guide connected to the comb body along its top face. The loading guide includes a series of L-shaped extensions protruding away from the comb body top face, each of these extensions is designed to align with spaces between sample wells constructed in the gel by the sample-well-forming teeth.

In both of these embodiments, when the comb is inserted into either a vertical gel electrophoresis cassette or a horizontal gel tray, with the sample-well-forming teeth projecting downward, the teeth make voids (i.e. wells) in the upper surface of a gel as the gel solution hardens. Upon hardening of the gel, the comb is removed and flipped, such that the loading guide is now pointed downward. The comb is then reinserted into the cassette with the loading guide being positioned above the wells to serve as a guide during the loading of liquid samples into the wells.

BRIEF DESCRIPTION OF THE DRAWINGS

A better understanding of the features and advantages of the present invention will be obtained by reference to the following detailed description that sets forth illustrative embodiments in which the principles of the invention are utilized, and the PATENT accompanying drawings, of which:

FIG. 6A is a front view of a well-forming and loading-guide comb in accordance with the present invention for use with horizontal gel electrophoresis apparatus.

FIG. 6B is a cross-sectional view, taken along line A—A of FIG. 6A of a well-forming and loading-guide comb in accordance with the present invention for use with horizontal gel electrophoresis apparatus.

FIG. 7 is a perspective view of a portion of the well-forming and loading-guide comb of FIGS. 6A and 6B.

DETAILED DESCRIPTION

Figure 1A:
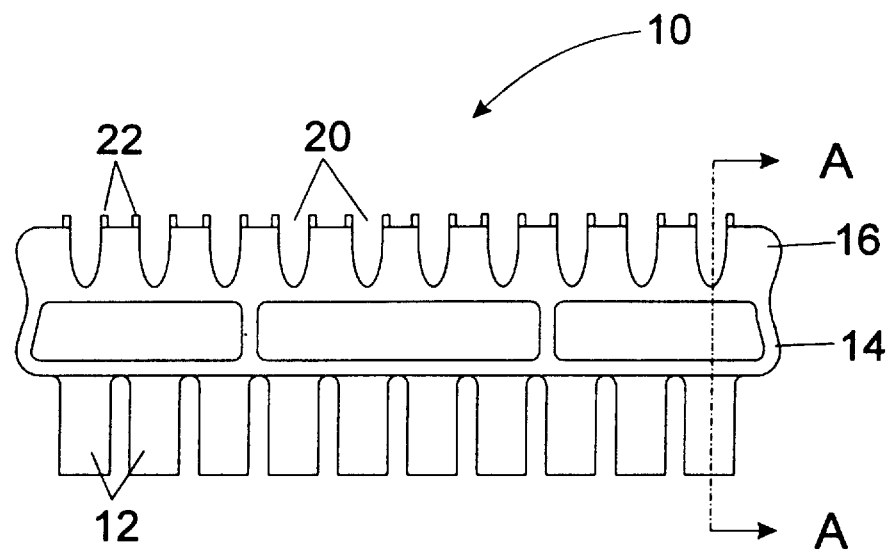
FIG. 1A is a front view of a well-forming and loading-guide comb in accordance with the present invention for use with vertical gel electrophoresis apparatus.
Figure 1B:
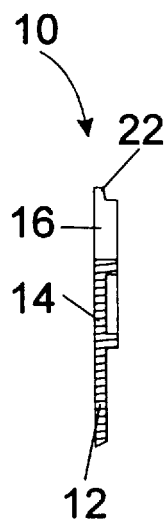
FIG. 1B is a cross-sectional view, taken along line A—A of FIG. 1A, of a well-forming and loading-guide comb in accordance with the present invention for use with vertical gel electrophoresis apparatus.

FIGS. 1A and 1B illustrate a well-forming and loading-guide comb 10 in accordance with the present invention.

Comb 10 includes a plurality of sample-well-forming teeth 12 connected along one edge of comb body 14. Loading guide 16 is connected to comb body 14 opposite sample-well-forming teeth 12.

Loading guide 16 includes loading alignment notches 20, each of which has an open end, and well alignment tabs 22. Loading alignment notches 20 are disposed in such a way that each and every loading alignment notch 20 is aligned with one of the sample well-forming teeth 12. Well alignment tabs 22 are located on either side of the open ends of loading alignment notches 20.

Figure 2:
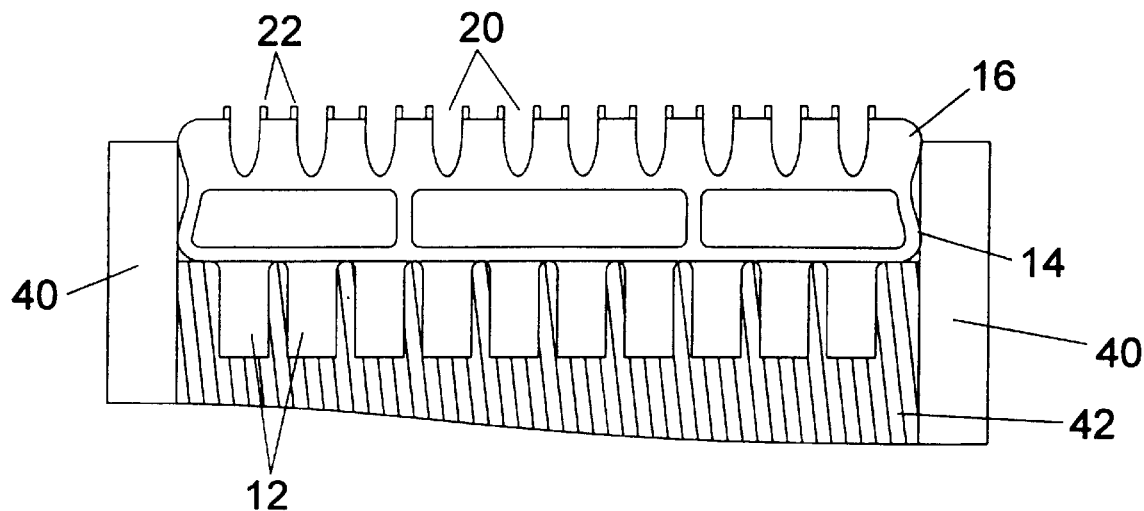
FIG. 2 is a front view of the well-forming and loading-guide comb of FIGS. 1A and B positioned in a vertical gel electrophoresis cassette (with the front plate removed for clarity) with the sample-well-forming teeth pointing downward and inserted into a gel.
Figure 3:
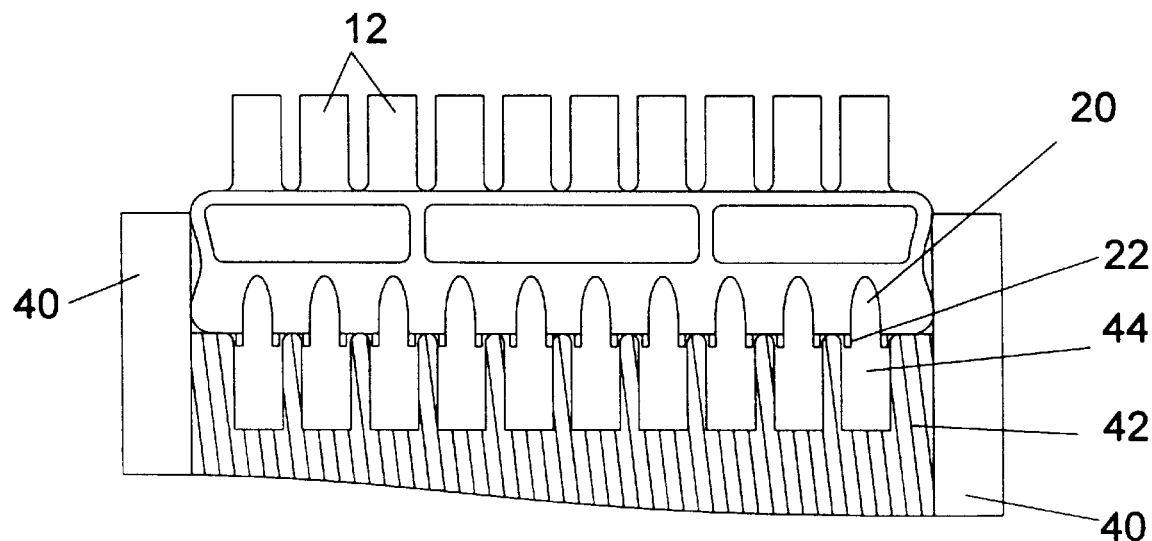
FIG. 3 illustrates the well-forming and loading-guide comb of FIGS. 1A and 1B positioned in a vertical gel electrophoresis cassette with the loading guide pointing downward and aligned with the sample wells.

As illustrated in FIGS. 2 and 3, comb body 14 is sized and shaped to fit between two opposing plates (not shown), of a vertical gel electrophoresis cassette, that are separated by two spacers 40. When used with sample-well-forming teeth 12 pointing downward, as shown in FIG. 2, comb 10 can form sample wells in a vertical gel 42. After vertical gel 42 has hardened, comb 10 is removed from the vertical gel electrophoresis cassette, thereby pulling sample-well-forming teeth 12 out of vertical gel 42, leaving sample wells 44 therein. Comb 10 is then rotated 180 degrees, such that loading guide 16 is now pointing downward, and reinserted into the vertical gel electrophoresis cassette as illustrated in FIG. 3. When loading guide 16 is introduced downwardly into vertical gel 42, loading alignment notches 20 are positioned immediately above sample wells 44. Well alignment tabs 22 aid in positioning and securely holding loading alignment notches 20 directly above sample wells 44 by protruding approximately 1 to 2 mm into the top of the sample wells. In this manner, loading alignment notches 20 of loading guide 16 provide easy guided access for loading samples into sample wells 44 via pipettes, syringes or other sample delivering instruments.

Figures 4A, 4B:
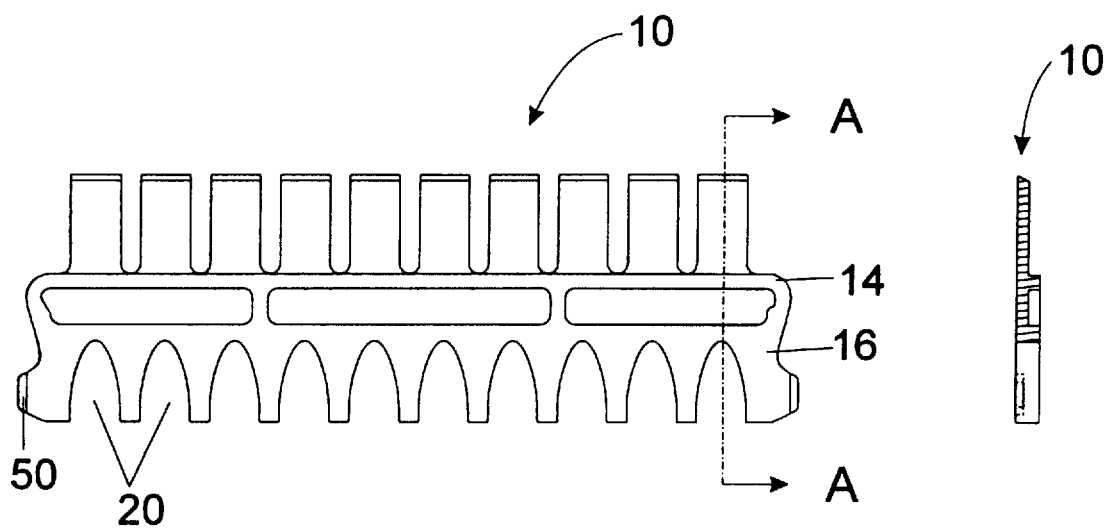
FIG. 4A is a front view of another embodiment of a well-forming and loading-guide comb in accordance with the present invention for use with vertical gel electrophoresis apparatus.
FIG. 4B is a cross-sectional view, taken along line A—A of FIG. 4A of a well-forming and loading-guide comb in accordance with the present invention for use with vertical gel electrophoresis apparatus.
Figure 5:
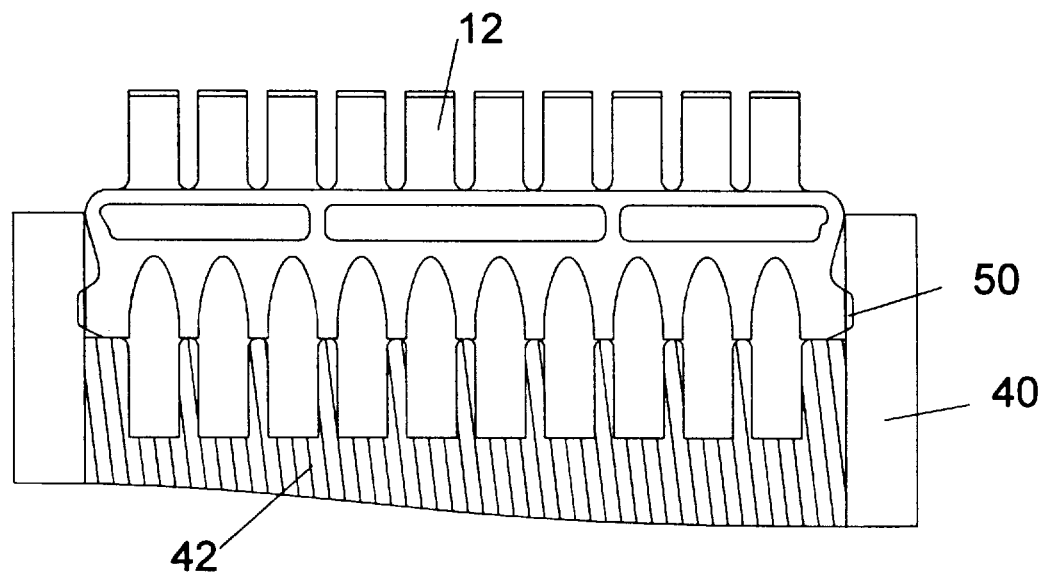
FIG. 5 is a front view of the well-forming and loading-guide comb of FIGS. 4A and 4B positioned in a vertical gel electrophoresis cassette with the loading guide pointing downward and aligned with the sample wells. (The front plate of the cassette is removed for clarity).

Alternative to the well alignment tabs, securely holding the comb in position within a vertical gel electrophoresis cassette during sample loading may also be accomplished by cassette guiding tabs 50 attached to the ends of comb 10, as illustrated in FIGS. 4A–5. Cassette guiding tabs 50 affix the comb in position by sliding along spacers 40 of the cassette.

FIGS. 6A, 6B and 7 illustrate another embodiment of comb 10, that is adapted for the use with horizontal electrophoresis trays. Comb 10 includes a plurality of sample-well-forming teeth 12 and loading guide 16. Sample-well-forming teeth 12 and loading guide 16 are connected along opposing faces of the comb body 14. Comb body 14 includes tray engagement tabs 30 at opposing ends of comb body 14. Loading guide 16 includes a series of L-shaped extensions protruding away from the comb body. Each of these L-shaped extensions is aligned with spaces between the sample-well-forming teeth 12.

Figure 8:
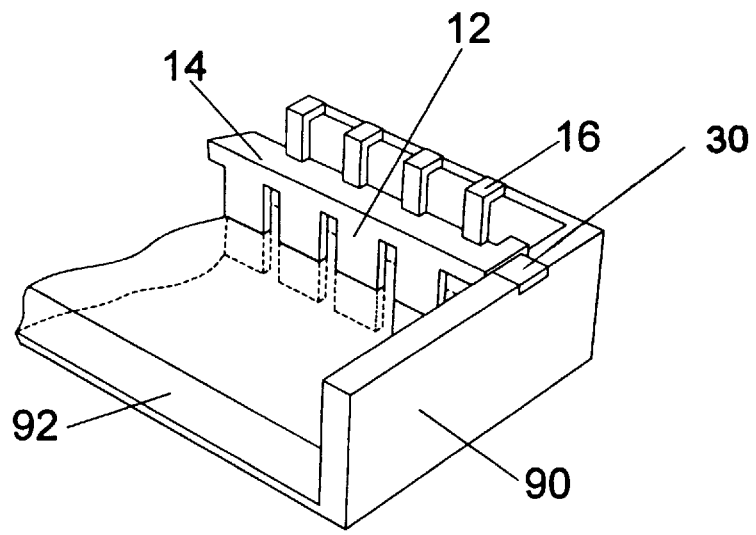
FIG. 8 is a perspective view of the well-forming and loading- guide comb of FIGS. 6A, 6B and 7 positioned in a horizontal electrophoresis tray with the sample-well-forming teeth pointing downward into the tray and gel.
Figure 9:
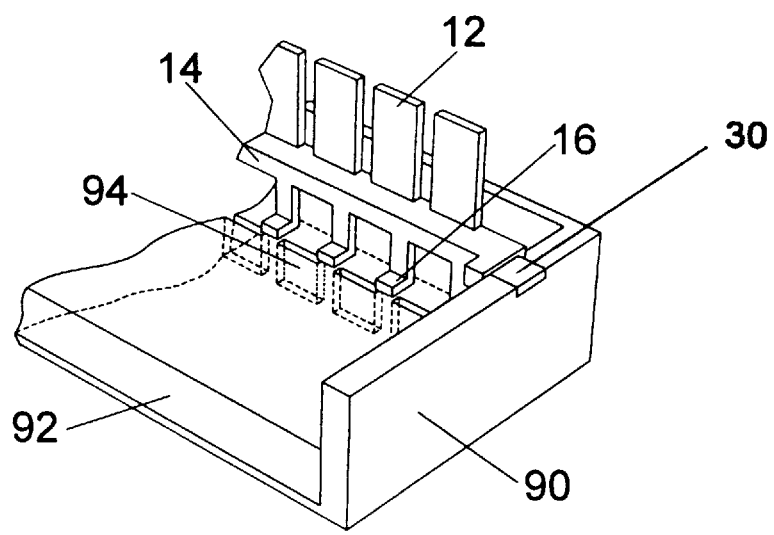
FIG. 9 is a perspective view of the well-forming and loading- guide comb of FIGS. 6A, 6B and 7 positioned in a horizontal electrophoresis tray with the loading guide pointing downward into the tray and above the gel surface.

As illustrated in FIGS. 8 and 9, comb body 14 is sized and shaped to engage a horizontal electrophoresis tray 90 via tray engagement tabs 30. Comb 10 is inserted in the horizontal electrophoresis tray 90 with the sample-well-forming teeth 12 extending downward into a gel 92, as shown in FIG. 8. After gel 92 has hardened, comb 10 is removed from horizontal electrophoresis tray 90, thereby lifting sample-well-forming teeth 12 out of the gel 92, leaving sample wells therein. Comb 10 is then rotated 180 degrees, such that the L-shaped extensions of loading guide 16 are now pointing downward, and re-engaged with horizontal electrophoresis tray 90 as illustrated in FIG. 9. As can be seen by reference to FIGS. 6A–7 and 9, the L-shaped extensions of the loading guide 16 are positioned directly over the surface of gel 92 in such a way that they straddle each of the sample wells 94. Therefore, the exact locations of the sample wells (i.e.

between two L-shaped extensions) can be easily detected. In this manner, the L-shaped extensions of loading guide 16 provide for easy guided access during the loading of samples into sample wells 94 via pipettes, syringes or other sample delivering instruments.

The well-forming and loading guide comb is most economically made by precision injection molding of inexpensive plastics, for example styrene, polyvinylchloride, PET, PETG or polycarbonate, the choice depending on the tendency of a particular gel matrix to adhere to the comb. For smaller quantities, the well-forming and loading-guide comb according to the present invention can also be produced by numerically controlled machine tools. Since the design of the invention is simple and inexpensive to manufacture, the comb can be discarded after a single use to avoid possible cross contamination of subsequent samples.

It should be understood that various alternatives to the embodiments of the invention described herein may be employed in practicing the invention. It is intended that the following claim define the scope of the invention and that structures within the scope of these claims and their equivalents be covered thereby.

What is claimed is:

1. A well-forming and loading-guide comb for electrophoresis gel, comprising:

a comb body having two opposing edges and ends, the comb body being of a predetermined size and shape adapted to fit between opposing plates of a vertical gel electrophoresis cassette;

a plurality of sample-well-forming teeth for forming sample wells in a gel, the plurality of sample-well-forming teeth connected along one opposing edge of the comb body; and a loading guide for guiding loading of samples in the sample wells, the loading guide disposed on the other opposing edge of the comb body.

2. The well-forming and loading-guide comb of claim 1, wherein the loading guide includes a plurality of loading alignment notches with open ends, the loading alignment notches aligned with the plurality of sample-well-forming teeth.

3. The well-forming and loading-guide comb of claim 2, wherein the loading guide includes a plurality of well-alignment tabs, each of the plurality of well-alignment tabs disposed on either side of the open end of the loading alignment notches.

4. The well-forming and loading-guide comb of claim 2, wherein the loading guide includes cassette guiding tabs attached to the ends of the comb body.

5. A well-forming and loading-guide comb for a comb body having a top face and a bottom face, the comb body being of a predetermined size and shape adapted to engage a horizontal gel tray;

a plurality of sample-well-forming teeth for forming sample wells in a gel, the plurality of sample-well-forming teeth connected to the comb body along the top face thereof; and a loading guide for guiding loading of samples in the sample wells, the loading guide connected to the comb body along the bottom face thereof.

6. The well-forming and loading-guide comb of claim 5, wherein the loading guide includes a plurality of L-shaped extensions, each of the L-shaped extensions aligned with spaces between the sample-well-forming teeth.

* * * * *

UNITED STATES PATENT AND TRADEMARK OFFICE
CERTIFICATE OF CORRECTION

PATENT NO. : 5,843,295
DATED : December 1, 1998
INVENTOR(S) : Urs Steiner et al.

It is certified that error appears in the above-identified patent and that said Letters Patent is hereby corrected as shown below:

Column 6, Line 17, Claim 5: after "for" insert --electrophoresis gel, comprising:--

Signed and Sealed this

Twenty-ninth Day of June, 1999

*Attest:*

Q. TODD DICKINSON

*Attesting Officer*     *Acting Commissioner of Patents and Trademarks*